United States Patent [19]
Eastmond et al.

[11] Patent Number: 5,834,620
[45] Date of Patent: Nov. 10, 1998

[54] AROMATIC POLYAMIDES AND POLYESTERS CONTAINING ORTHO-ETHER GROUPS

[75] Inventors: Geoffrey Charles Eastmond, Wirral; Jerzy Paprotny, Liverpool, both of United Kingdom

[73] Assignee: University of Liverpool, Liverpool, England

[21] Appl. No.: 969,871

[22] Filed: Nov. 14, 1997

Related U.S. Application Data

[62] Division of Ser. No. 664,630, Jun. 18, 1996.

[51] Int. Cl.$^6$ .................................................. C07C 69/76
[52] U.S. Cl. ................................. 560/8; 528/98; 528/102; 528/110; 528/111; 528/211; 528/401; 560/19; 560/21; 560/23; 560/76; 568/579; 568/626; 568/630
[58] Field of Search ............................. 528/98, 102, 110, 528/111, 211, 401; 560/8, 19, 21, 23, 76; 568/579, 626, 630

[56] References Cited

U.S. PATENT DOCUMENTS

| | | | |
|---|---|---|---|
| 4,229,566 | 10/1980 | Evers et al. | 528/185 |
| 5,153,306 | 10/1992 | Matsuo et al. | 528/206 |
| 5,258,485 | 11/1993 | Matsuo et al. | 528/206 |
| 5,340,904 | 8/1994 | Yang et al. | 528/185 |
| 5,514,769 | 5/1996 | Tan et al. | 528/322 |

OTHER PUBLICATIONS

R. C. Evers, et al., *Macromolecules,* 14, 925–930, 1981.

Yang et al., *Makromol. Chem.,* 194, 1595–1605, 1993.

*Primary Examiner*—Samuel A. Acquah

[57] ABSTRACT

Described herein are polyesters and polyamides which contain repeat units derived from novel dicarboxylic acids comprising arylene groups having ortho ethers substituted thereon. Also disclosed are novel compounds from which these polymers can be made. The polymers are especially useful for molding resins and coatings.

8 Claims, No Drawings

AROMATIC POLYAMIDES AND POLYESTERS CONTAINING ORTHO-ETHER GROUPS

This is a divisional application of Ser. No. 08/664,630, filed on Jun. 18, 1996.

FIELD OF THE INVENTION

Described herein are novel polyesters and polyamides derived from aromatic dicarboxylic acids, or their reactive equivalents, which contain paired ether groups ortho in position to one another on an aromatic portion of such polymers. Also disclosed are novel monomers from which these polymers can be made.

TECHNICAL BACKGROUND

It is well known that polyesters and polyamides are important items of commerce, useful as fibers, molding resins, in coatings, for films, and many other uses. Therefore, new polyesters or polyamides with useful properties are constantly being sought. For example, many polyesters and polyamides are not readily soluble in organic solvents, making them less useful in solvent-based coatings.

U.S. Pat. No. 4,229,566 and R. C. Evers, et al., Macromolecules, vol. 14, p. 925–930 (1982) describe the preparation of certain dinitriles which are subsequently used to prepare polybenzoxazoles. No polyesters or polyamides are described in these references.

Many of the polyamides and polyesters claimed herein, while having various uses, are readily soluble in organic solvents, making them especially useful for coatings.

SUMMARY OF THE INVENTION

This invention concerns a polymer comprising the repeat unit

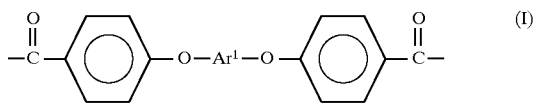

wherein $Ar^1$ is arylene or alkyl- or halo-substituted arylene and in which said ether oxygen atoms are substituted on $Ar^1$ in ortho positions; and, furthermore, said polymer comprises at least one other repeat unit such that the polymer is a polyester, a polyamide or a poly(amide-ester).

The invention also concerns a compound of the formula

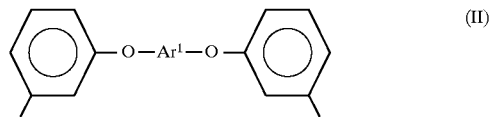

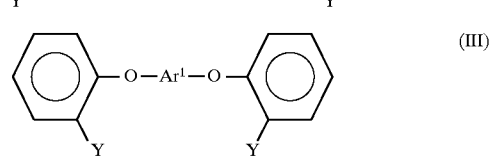

or

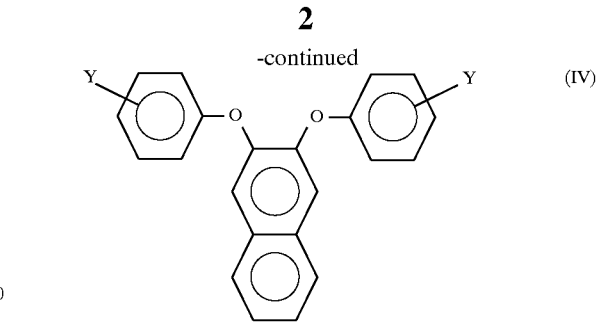

wherein:
$Ar^1$ is o-phenylene, alkyl substituted o-phenylene, or halogen substituted o-phenylene (wherein "o" indicates ortho);
Y is —CN, —CO$_2$H, CO$_2$R$^1$ or COX;
$R^1$ is hydrocarbyl containing 1 to 20 carbon atoms; and
X is halogen.

DETAILS OF THE INVENTION

In the polymers according to the present invention, the above-described repeat unit (I) is part of a polyester, polyamide or poly(amide-ester). The other repeat unit(s) in the polymer may be one or more of —O—R$^2$—O— (V), —R$^3$N—R$^2$—NR$^3$— (VI), or —O—R$^2$—NR$^3$— (VII), which are derived, respectively, from a diol, diamine or hydroxyamine. In these formulas, each R$^2$ is independently hydrocarbylene or substituted hydrocarbylene, and each R$^3$ is independently hydrogen, hydrocarbylene, or substituted hydrocarbylene. By hydrocarbylene is meant a univalent radical containing only carbon and hydrogen. Preferably, said hydrocarbylenes have 1 to 10 carbon atoms. By "substituted" herein is meant that a specified radical may contain one or more substituents which do not interfere with the formation of the polymer. Preferably, R$^2$ is arylene and, more preferably, it is phenylene, especially o-, m- or p-phenylene. R$^3$ is preferably hydrogen. Although other repeat units may also be present (for example, repeat units derived from other dicarboxylic acids, diols, diamines and/or hydroxyamines), it is preferred that one or more of the repeat units corresponding to (II), (III) and (IV) alternate with one or more of the repeat units (V), (VI), and (VII). It is also preferred that only one of the repeat units corresponding to (II), (III) or (IV) and/or only one of the repeat units (V), (VI) or (VII) are present in any particular polymer. Preferably, at least 80 percent, more preferably at least 90 percent, on a molar basis, of the total repeat units in the polymer are selected from those according to the above formulas (I) to (VII).

In repeat unit (I), $Ar^1$ is arylene. By arylene herein is meant a divalent radical containing at least one aromatic ring, preferably having 6 to 10 aromatic ring carbon atoms, in which the free valencies of the radical are to aromatic ring carbon atoms. In this case, the ether groups are ortho to one another on $Ar^1$, that is, each of the ether oxygen atoms are bound to carbon atoms adjacent to one another in an aromatic ring. Preferred arylene groups $Ar^1$ are o-phenylene and 2,3-naphthylene. The arylene groups $Ar^1$ may be substituted with one or more alkyl groups and/or one or more halogens. Preferred alkyl groups preferably have 1 to 10 carbon atoms, more preferably, 1 to 6 carbon atoms. Especially preferred alkyl groups are methyl and t-butyl. Fluorine is a preferred halogen. Preferred substituted arylene groups $Ar^1$ are 3,4-di-t-butyl-o-phenylene, 3-fluoro-o-phenylene, and 4-t-butyl-o-phenylene.

The polyesters, polyamides and poly(amide-esters) described herein can be made by standard methods known to the artisan. See, for instance, Examples 25–29 below. These polymers are useful for molding resins for making parts, such as electronic connectors, for fibers, for films, and especially for coatings, since many of them are soluble in organic solvents.

For compounds (II) and (III) herein, the same substitution of the o-phenylene group $Ar^1$ is preferred as for the $Ar^1$ in repeat unit (I). For compounds (II), (III) and (IV), it is preferred that both of Y are the same. It is also preferred that X is chlorine or $R^1$ is an alkyl group containing 1 to 6 carbon atoms. In compound (IV), it is preferred that both of Y be in the same positions on their respective phenyl rings relative to the ether oxygen atoms bound to those phenyl rings, i.e., that (IV) be symmetrical.

Compounds of the formulas (II), (III) and (IV) can be made by methods illustrated in the Examples herein provided. The various Y groups may be interconverted to one another by methods known in the art. Compounds (II), (III) and (IV) are useful as monomers for making the polymers herein described, or may be used as intermediates for making monomers for the polymers herein described.

In the Examples that follow, the following abbreviations are used (other abbreviations are defined in the Examples themselves or the Tables that follow):

DMAC—N,N-dimethylacetamide
DMF—N,N-dimethylformamide
NMP—N-methylpyrrolidone
THF—tetrahydrofuran

EXAMPLE 1

Preparation of 1,2-bis-(4-cyanophenoxy) benzene

In a three-necked flask equipped with a magnetic stirring bar, thermometer and a Dean-Stark trap connected to a reflux condenser, there was placed 11.0 g (0.1 mole) of catechol, 150 mL NMP, 24.2 g (0.2 mole) of 4-fluorobenzonitrile, 26 g anhydrous potassium carbonate and 30 mL toluene. The contents of the flask, while stirred, were brought to the boil and water was collected in the Dean-Stark trap. The temperature in the flask was 140° C. Boiling was continued for 6 hours after the evolution of water ceased and toluene was then distilled off, while the temperature in the flask rose to 200° C. The contents were poured into 1.5 l of cold, stirred water. The precipitate (brown mud) was filtered off and washed several times with deionised water. While wet, with water, the product was recrystallized from methanol, yielding 24.8 g (79.5%) of light brown crystals. The crystals were purified by two consecutive recrystallizations with decolourizing charcoal from methanol/water (5:1) to yield 11.6 g of snow-white crystals and 3.44 g of off-white second-crop crystals of the title compound having the formula:

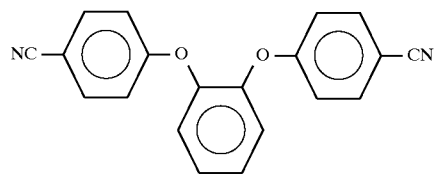

The melting point was 116.7°–117.3° C. The elemental analysis for $C_2OH_{12}N_2O_2$ was calc.: C, 76.91%, H, 3.87%, N, 8.97%, found: C, 76.90%, H, 3.84%, N, 8.94%.

EXAMPLE 2

Preparation of 1.2-bis-(3-cyanophenoxy) benzene

The compound 1,2-bis(3-cyanophenoxy)benzene was synthesized from 3-flourobenzonitrile and catechol by a procedure identical to that used to prepare 1,2-bis(4-cyanophenoxy)benzene according to Example 1 above. The crude product was in the form of brown crystals which were purified by two consecutive recrystallizations with decolourizing charcoal from methanol/water (5:1) to give 70.44% yield of the title compound with the formula:

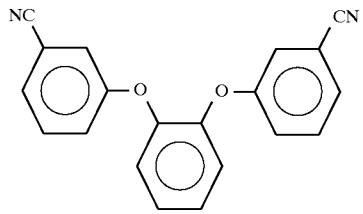

The melting point was 99.2°–99.7° C. The elemental analysis for $C_2OH_{12}N_2O_2$ was calc.: C, 76.91%, H, 3.87%, N, 8.97%, found: C, 77.17%, H, 3.81%, N, 8.93%.

EXAMPLE 3

Preparation of 1,2-bis-(2-cyanophenoxy) benzene

The compound 1,2-Bis(2-cyanophenoxy)benzene was synthesized in the same manner as for 1,2-bis-(4-cyanophenoxy)benzene according to Example 1 above, but from 2-fluorobenzonitrile and catechol, except that the synthesis was performed in DMF at 125° C. and over a period of 10 hours. The precipitate was filtered off and washed several times with deionised water. The white product was recrystallized from methanol/water (8:1). The yield was 84.6% of the title compound with the formula:

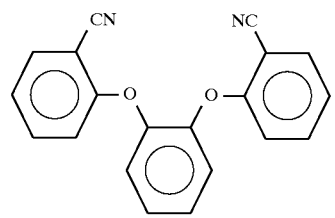

The melting point was 105.4°–105.8° C. The elemental analysis for $C_2OH_{12}N_2O_2$ was calc.: C, 76.91%, H, 3.87%, N, 8.97%, found: C, 77.07%, H, 3.85%, N, 9.02%.

EXAMPLE 4

Preparation of 2,3-bis-(4-cyanophenoxy) naphthalene

To prepare 2,3-bis-(4-cyanophenoxy)naphthalene, 2,3-dihydroxynaphthalene was reacted with 4-fluorobenzonitrile according to the procedure described in Example 1. The product was recrystallized from ethanol/water (15:1). The yield was 89.22% of the title compound with the formula:

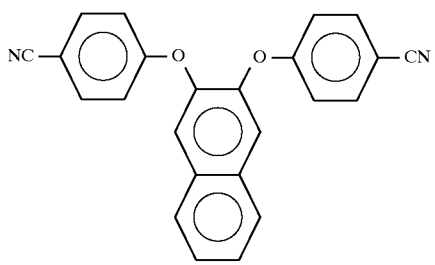

The melting point was 137.5°–138.2° C. The elemental analysis for $C_{24}H_{14}N_2O_2$ was calc. C, 79.54%, H, 3.89%, N, 7.73%, found: C, 79.59%, H, 3.88%, N, 7.70%.

EXAMPLE 5

Preparation of 2,3-bis-(3-cyanophenoxy) naphthalene

To prepare 2,3-bis-(3-cyanophenoxy)naphthalene, 2,3-dihydroxynaphthalene was reacted with 3-fluoro-nitrile according to the procedure described in Example 1. The product was recrystallized from ethanol. The yield was 51.4% of the title compound with the formula:

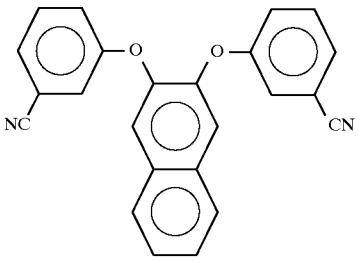

The melting point was 157°–158° C. The elemental analysis for $C_{24}H_{14}N_2O_2$ was calc.: C, 79.54%, H, 3.89%, N, 7.73%, found: C, 79.77%, H, 3.88%, N, 7.71%.

EXAMPLE 6

Preparation of 1,2-bis-(4-cyanophenoxy)-3-fluorobenzene

The compound 1,2-bis-(4-cyanophenoxy)-3-fluorobenzene was prepared according to the procedure described in Example 1 by reacting 4-fluorobenzonitrile with 1,2-dihydroxy-3-fluorobenzonitrile. The product was recrystallized from ethanol/water (4:1). The yield was 89.4% of the title compound with the formula:

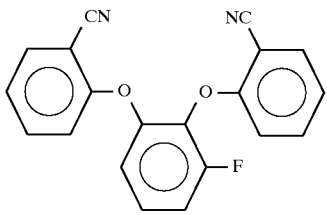

The melting point was 98°–99° C. The elemental analysis for $C_{20}H_{11}FN_2O_2$: was calc: C, 72.72%, H, 3.35%, N, 8.48%, found: C, 72.39%, H, 3.28%, N, 8.38%.

EXAMPLE 7

Preparation of 1,2-bis-(4-cyanophenoxy)-3.5-di-tert-butylbenzene

The compound 4-fluoronitrile was reacted with 1,2-dihydroxy-3,5-di-tert-butyl benzene according to the procedure of Example 1. The product was recrystallized from ethanol to give 90.0% yield of the compound with the formula:

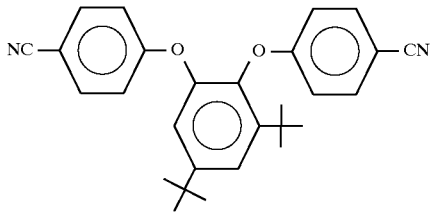

The melting point was 187°–188° C. The elemental analysis for $C_{26}H_{28}N_2O_2$: was calc: C, 79.21%, H, 6.64%, N, 6.60%, found: C, 79.20%, H, 6.62%, N, 6.58%.

EXAMPLE 8

Preparation of 1,2-bis-(3-cyanophenoxy)-3,5-di-tert-butylbenzene

The compound 3-fluoronitrile was reacted with 1,2-dihydroxy-3,5-di-tert-butylbenzene according to the procedure of Example 1. The product was recrystallized from methanol. The yield was 52.38% of the title compound with the formula:

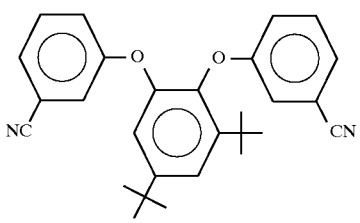

The melting point was 118°–119° C. The elemental analysis for $C_{26}H_{28}N_2O_2$: was calc: C, 79.21%, H, 6.64%, N, 6.60%, found: C, 79.38%, H, 6.67%, N, 6.58.

EXAMPLE 9

Preparation of 1,2-bis-(2-cyanophenoxy)-3,5-di-tert-butylbenzene

The compound 1,2-bis-(2-cyanophenoxy)-3,5-di-tert-butylbenzene was prepared, according to the procedure of Example 1, by reacting 2-fluorobenzonitrile with 1,2-dihydroxy-3,5-di-tert-butyl benzene. The product was recrystallized from ethanol to give a 90.1% yield of the title compound with the formula:

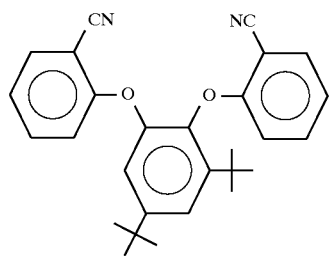

The melting point was 172°–173° C. The elemental analysis for $C_{26}H_{28}N_2O_2$: was calc: C, 79.21%, H, 6.64%, N, 6.60%, found: C, 79.20%, H, 6.66%, N, 6.57%.

EXAMPLE 10

Preparation of 1,2-bis-(4-cyanophenoxy)-4-tert-butylbenzene

The compound 4-fluorobenzonitrile was reacted with 4-tert-butylcatechol according to the procedure of Example 1. The product was recrystallized from methanol/water (3:1) to give a 96.1% yield of the title compound with the formula:

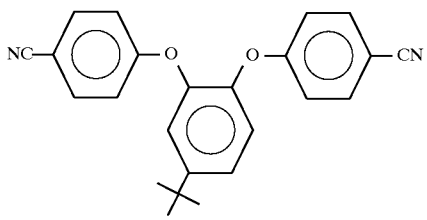

The melting point was 119°–120° C. The elemental analysis for $C_{23}H_{20}N_2O_2$: was calc: C, 78.24%, H, 5.47%, N, 7.60%, found: C, 78.44%, H, 5.46%, N, 7.58%.

EXAMPLE 11

Preparation of 1,2-bis-(4-carboxyphenoxy) benzene (POP diacid)

In a round-bottomed flask was placed 11.5 g (0.0368 mol) of 1,2-bis(4-cyanophenoxy)benzene, prepared as described in Example 1, together with 20 g (0.35 mol) of potassium hydroxide, 20 mL water and 40 mL methanol. The mixture was refluxed for 16 hours until the evolution of ammonia ceased. The solution was then diluted to 1.0 l with water and was acidified with concentrated HCl to pH 1.5. The white diacid was filtered off, washed with water, and while wet, was recrystallized from 300 mL acetic acid to yield 10.84 g (84.16% yield) of snow-white crystals of 1,2-bis-(4-carboxyphenoxy) benzene with the formula:

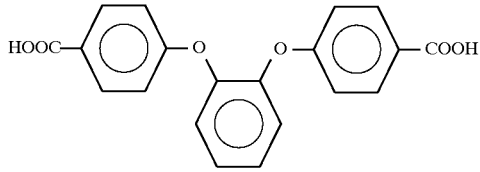

The product had a melting point of 257°–258° C. The elemental analysis for $C_{20}H_{14}O_6$: was calc: C, 68.57%, H, 4.03%, found: C, 68.57%, H, 4.02%.

EXAMPLE 12

Preparation of 1,2-bis-(3-carboxyphenoxy) benzene (MOM diacid)

The title compound was prepared by hydrolysing 1,2-bis (2-cyanophenoxy)benzene (prepared as in Example 2) according to the procedure of Example 11. The yield was 99.28% of 1,2-bis-(3-carboxyphenoxy) benzene with the formula:

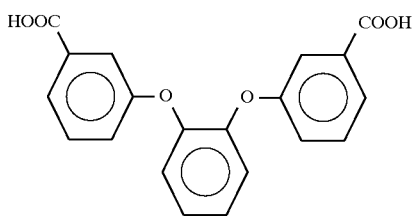

The product had a melting point of 265°–267° C. The elemental analysis for $C_{20}H_{14}O_6$: was calc: C, 68.57%, H, 4.03%, found: C, 668.49%, H, 3.99%.

EXAMPLE 13

Preparation of 1,2-bis-(2-carboxyphenoxy) benzene (OOO diacid)

The title compound was prepared by hydrolysing 1,2-bis (2-cyanophenoxy)benzene (prepared in Example 3) according to the procedure of Example 11. The product was recrystallized from THF/cyclohexane (1:2) to give a 89.53% yield of 1,2-bis-(2-carboxyphenoxy) benzene with the formula:

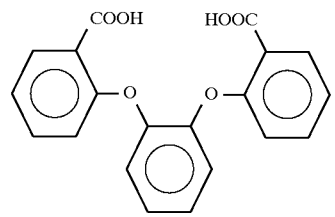

The product had a melting point of 184°–185° C. The elemental analysis for $C_{20}H_{14}O_6$: was calc: C, 68.57%, H, 4.03%, found: C, 68.60%, H, 3.97%.

EXAMPLE 14

Preparation of 2,3-bis-(4-carboxyphenoxy) naphthalene (PNOP diacid)

The title compound was prepared by hydrolysing 2,3-bis-(4-cyanophenoxy)naphthalene (prepared in Example 4) according to the procedure of Example 11. The product was recrystallized from acetic acid to give a 87.4% yield of 2,3-bis-(4-carboxyphenoxy)naphthalene with the formula:

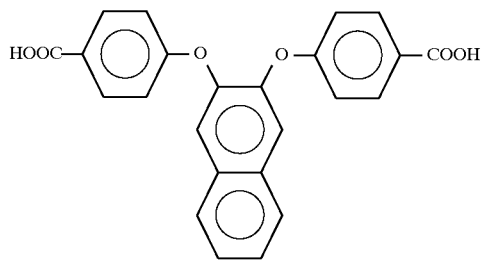

The product, after sublimation, had a melting point of 282°–285° C. The elemental analysis for $C_{24}H_{16}O_6$: was calc: C, 72.00%, H, 4.03%, found: C, 71.53%, H, 3.93%.

EXAMPLE 15

Preparation of 2,3-bis-(3-carboxyphenoxy) naphthalene (MNOM diacid)

The title compound was prepared by hydrolysing 2,3-bis-(3-cyanophenoxy)naphthalene (prepared in Example 5) according to the procedure of Example 11. The product was recrystallized from acetic acid to give a 88.5% yield of 2,3-bis-(3-carboxyphenoxy)naphthalene with the formula:

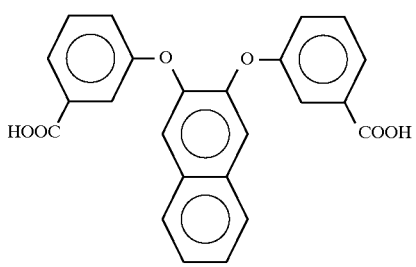

The product, after sublimation, had a melting point of 260°–262° C. The elemental analysis for $C_{24}H_{16}O_6$: was calc: C, 72.00%, H, 4.03%, found: C, 72.14%, H, 3.98%.

EXAMPLE 16

Preparation of 1,2-bis-(2-carboxyphenoxy)-3-fluorobenzene (M3FOM diacid)

The title compound was prepared by hydrolysing 1,2-bis-(4-cyanophenoxy)-3-fluorobenzene (prepared in Example 6) according to the procedure of Example 11. The product was recrystallized from acetic acid/water (3:2) to give a 92.3% yield of 1,2-bis-(2-carboxyphenoxy)-3-fluorobenzene with the formula:

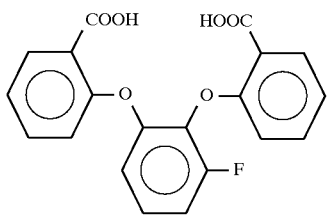

The product, after sublimation, had a melting point of 207°–210° C. The elemental analysis for $C_{20}H_{13}FO_6$: was calc: C, 65.22%, H, 3.55%, found: C, 65.15%, H, 3.58%.

EXAMPLE 17

Preparation of 1,2-bis-(4-carboxyphenoxy)-3,5-di-tert-butylbenzene (P35DTBOP diacid)

The title compound was prepared by hydrolysing 1,2-bis-(4-cyanophenoxy)-3,5-di-tert-butylbenzene (prepared in Example 7) according to the procedure of Example 11. The product was recrystallized from acetic acid to give a 87% yield of 1,2-bis-(4-carboxyphenoxy)-3,5-di-tert-butylbenzene with the formula:

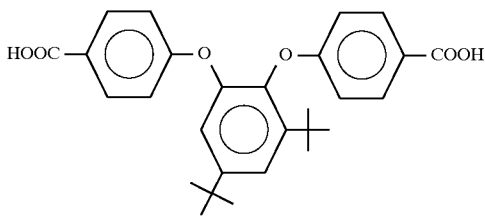

The product had a melting point of 251°–252° C. The elemental analysis for $C_{26}H_{30}O_6$: was calc: C, 72.70%, H, 6.53%, found: C, 72.83%, H, 6.53%.

EXAMPLE 18

Preparation of 1,2-bis-(2-carboxyphenoxy)-3,5-di-tert-butylbenzene (O35DTBOO diacid)

The title compound was prepared by hydrolysing 1,2-bis-(2-cyanophenoxy)-3,5-di-tert-butylbenzene (prepared in Example 9) according to the procedure of Example 11; the hydrolysis proceeded extremely slowly. The product was recrystallized from acetic acid to yield of 1,2-bis-(2-carboxyphenoxy)-3,5-di-tert-butylbenzene with the formula:

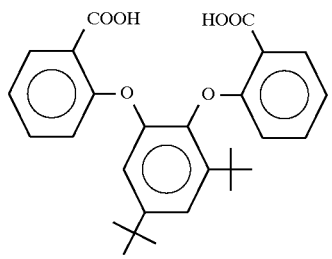

The product, after sublimation, had a melting point of 265°–267° C. The elemental analysis for $C_{26}H_{30}O_6$: was calc: C, 72.70%, H, 6.53%, found: C, 72.81%, H, 6.53%.

EXAMPLE 19

Preparation of 1,2-bis-(4-carboxyphenoxy)-4-tert-butylbenzene (P3TBOP diacid)

The title compound was prepared by hydrolysing 1,2-bis-(4-cyanophenoxy)-4-tert-butylbenzene (prepared in Example 10) according to the procedure of Example 11. The product was recrystallized from acetic acid/water (3:2) to give a 90.6% yield of 1,2-bis-(4-carboxyphenoxy)-4-tert-butylbenzene with the formula:

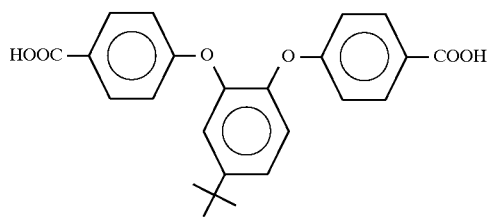

The product, after sublimation, had a melting point of 231°–232° C. The elemental analysis for $C_{23}H_{22}O_6$: was calc: C, 70.92%, H, 5.54%, found: C, 70.99%, H, 5.47%.

EXAMPLE 20

Preparation of 1,2-bis-(4-carboxyphenoxy)-benzene dichloride (POP diacid chloride)

Ten mmol of the diacid 1,2-bis-(4-carboxyphenoxy) benzene, prepared in Example 11, was boiled under reflux in a nitrogen atmosphere with about 20 mmol of thionyl chloride for 2 hours. The reflux condenser was protected with a calcium chloride guard tube. Excess thionyl chloride was distilled off, heating with a water bath, under vacuum which was finally reduced to 0.2–0.5 torr. The resulting, crude acid chloride was then dissolved in 50 mL cyclohexane of which about one third was then distilled off and the residual solution left to crystallize. The crude acid chloride was sublimed from a thoroughly degassed melt at about 200° C. at 0.5 torr pressure. The yield was 81.4% of diacid chloride with the formula:

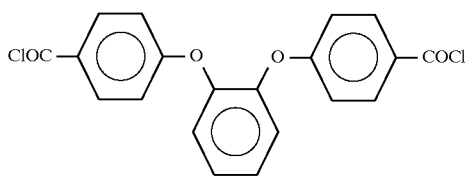

The product, after sublimation, had a melting point of 93°–95° C. The elemental analysis for $C_{20}H_{12}Cl_2O_4$ was calc: C, 62.03%, H, 3.12%, Cl, 18.31%, found: C, 61.77%, H, 3.12%, Cl, 17.54%.

EXAMPLE 21

Preparation of 1,2-bis-(3-carboxyphenoxy)-benzene dichloride (MOM diacid chloride)

10 mmol of the diacid 1,2-bis-(3-carboxyphenoxy)-benzene, prepared in Example 12, was reacted with of thionyl chloride according to the procedure described in Example 20. The result was a 63.3% yield of acid chloride of formula:

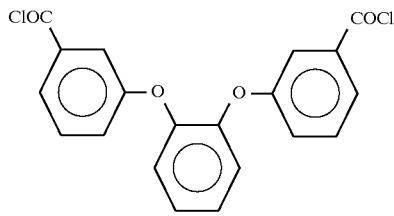

The product, after sublimation, had a melting point of 74°–76° C. The elemental analysis for $C_{20}H_{12}Cl_2O_4$ was calc: C, 62.03%, H, 3.12%, Cl, 18.31%, found: C, 61.89%, H, 3.12%, Cl, 17.47%.

EXAMPLE 22

Preparation of 2,3-bis-(4-carboxyphenoxy) naphthalene dichloride (PNOP diacid chloride)

The compound 2,3-bis-(4-carboxyphenoxy)naphthalene dichloride was prepared by reacting 2,3-bis-(4-carboxyphenoxy)napthalene with thionyl chloride according to the procedure of Example 20. After initial crystallization, the product was again recrystallized from cyclohexane/toluene (1;1) to give a 96.5% yield of the title compound with the formula:

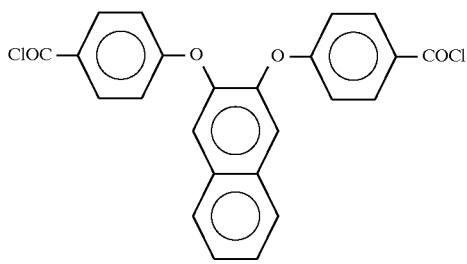

The product had a melting point of 113°–116° C. The elemental analysis for $C_{24}H_{14}Cl_2O_4$: was calc: C, 66.22%, H, 2.77%, Cl, 16.29%, found: C, 66.77%, H, 3.32%, Cl, 15.35%.

EXAMPLE 23

Preparation of 1,2-bis-(4-carboxyphenoxy)-3,5-di-tert-butylbenzene dichloride (P35DTBOP diacid chloride)

The compound 1,2-bis-(4-carboxyphenoxy)-3,5-di-tert-butylbenzene dichloride was prepared from 1,2-bis-(4-carboxyphenoxy)-3,5-di-tert-butylbenzene according to the procedure of Example 20. After initial crystallization, the product was recrystallized from a minimum of cyclohexane to give a 81.8% yield of product with the formula:

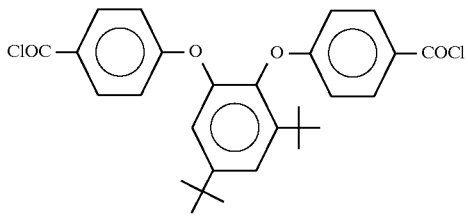

The product had a melting point of 157°–160° C. The elemental analysis for $C_{26}H_{28}Cl_2O_4$: was calc: C, 67.33%, H, 5.65%, Cl, 14,19%, found: C, 67.63%, H, 5.82%, Cl, 13.62%.

EXAMPLE 24

Preparation of 1,2-bis-(4-carboxyphenoxy)-4-tert-butylbenzene dichloride (P3TBOP diacid chloride)

The procedure of Example 23 was used to prepare 1,2-bis-(4-carboxyphenoxy)-4-tert-butylbenzene dichloride from 1,2-bis-(4-carboxyphenoxy)-4-tert-butylbenzene and thionyl chloride to give a 65.6% yield of the title compound with the formula:

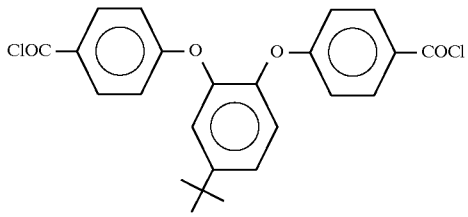

The product had a melting point of 107°–110° C. The elemental analysis for $C_{23}H_{20}Cl_2O_4$: was calc: C, 65.02%, H, 4.54%, Cl, 15.99%, found: C, 65.54%, H, 4.80%, Cl, 17.27%.

Syntheses of Polyamides

Poly(ether amide) copolymers, derived from the catechol-based diacids synthesized in Examples 11–19, were synthesized by different procedures, as described in full in Examples 25 and 26. Any variations with respect to the procedures are cited in the subsequent specific examples. The phosphorylation technique (Examples 25a–e), described by Yamazaki, N., Higashi, F. and Kawabata, J., J. Polym. Sci., Polym. Chem. Ed., 1974 vol. 12, at 2149; Higashi, F., Ogata, S. I. and Aoki, Y., J. Polym. Sci., Polym. Chem. Ed., 1982, vol. 20, at 2081, was used to demonstrate the feasibility of preparing polyamides from the several acids mentioned, but, under the reaction conditions used, results in low molecular weight polymer. Polymers of higher molecular weight were prepared by first converting the acids to acid chlorides, as described in Examples 20–24, and reacting the acid chloride with a diamine (Examples 26a–p); specific examples are cited in Table 2.

The diamines used in the several syntheses are identified by a code in the titles of the Examples and by their structural formulae in Table 1. The characterization details of the poly(ether-amides) prepared are given in Tables 2 and 3 and, in these and other tables, the diacids used are identified by a code given with the systematic names of the anhydrides in Examples 25–29.

EXAMPLES 25(A–E)

Preparations of Polymers by the Phosphorylation Technique

EXAMPLE 25A

Preparation of Polymer from 1,2-bis-(4-carboxyphenoxy) benzene (POPCAc) and p-Phenylene Diamine (PPD)

In 13 mL of anhydrous NMP (under a nitrogen atmosphere) was dissolved 0.6 g of anhydrous calcium chloride and 0.2 g of lithium chloride. Then 4 mL of anhydrous pyridine was added, followed by 0.70 g of 1,2-bis-(4-carboxyphenoxy)benzene (2 mmol) and 2 mmol of para-phenylene diamine. The mixture was stirred under nitrogen and 2 mL of triphenyl phosphite was added and the temperature was raised to 105° C. for 5 hours when an additional 1 mL of triphenyl phosphite and 1 mL pyridine were added and the mixture was stirred at 110° C. The viscous liquid was then poured into 300 mL of methanol/water (80/20). The polymer was filtered off and extracted with boiling methanol for 1 hour. The yield of polymer was 0.78 g. The M. Wt. (kg mol$^{-1}$) was 39, the Tg (°C.) was 210 and the TGA weight loss was 98% in the temperature range 390–643.

The same procedure was used for Examples 25B–E.

EXAMPLES 26A–O

Preparations of Polymers Using Preformed Acid Chloride

These were performed using the typical procedure of Example 26A.

EXAMPLE 26A

Preparation of Polymers from 1,2-bis-(4-carboxyphenoxy) Benzene Dichloride and p-Phenylene Diamine One mmol of PPD was dissolved in 7 mL DMAC containing 8.7% CaCl$_2$ and 0.7 mL pyridine. The mixture was cooled to −14° C. and solid 1,2-bis-(4-carboxyphenoxy) benzene dichloride (1 mmol) was added. The mixture was stirred vigorously for 2.5 hr during which period it became very viscous. The mixture was then kept overnight at ~0° C. in a fridge, followed by 24 hr at room temperature. The polymer was precipitated into MeOH/H$_2$O, twice extracted with boiling MeOH and dried.

Syntheses of Aromatic Polyesters and Copolyesters

Polyarylates, derived from the catechol-based diacids synthesized in Examples 11–19, were synthesized by different procedures as described in full in Examples 27 and 28; any variations for each of the procedures are cited in the subsequent specific examples.

EXAMPLES 27

Preparation of Polyarylates by Transesterification

Three mmol of a diacid and 3.0 mmol of a diol diacetate together with 0.002 g of dibutyltin oxide were melted and stirred under nitrogen with 3–4 g of m-terphenyl. Within 1–1.5 hr the temperature was raised to 340° C. The reaction was run for 5–8 hours while gradually raising the temperature to 370°–380° C. After cooling to about 110° C. the viscous melt was poured into acetone or into toluene/methanol (40/60). The polymer was filtered off and extracted with boiling acetone or methanol and dried. Yields of polymer were about 80%. The polymers and copolymers were subjected to preliminary testing for solubility and for ability to pull fibres from the melt.

EXAMPLE 28

Preparation of Polyarylates by Reaction of Acid Chloride

In order to form polyesters using acid chlorides, 1.0 mmol of acid chloride and 1.0 mmol of diol were refluxed together in dichlorobenzene for 3 hours. The polymer was isolated by precipitation into methanol, was extracted with methanol and dried. An example is given in Table 3.

EXAMPLE 29

Preparation of Copolyarylates by Transesterification

Exactly the same reaction conditions were applied as for Example 27, except that hdyroxybenzoic acid was added in different proportions such that there was an overall stoichiometric balance of acid and hydroxyl, or protected hydroxyl functionality. Details of Examples are given in Table 4.

EXAMPLE 30

Synthesis of 1,2-bis(4-aminophenoxy)benzene (POP Amine)

A. Synthesis of Intermediate 1,2-bis(4-nitrophenoxy)-benzene

In a three-necked round-bottomed flask equipped with nitrogen inlet, thermometer and Dean-Stark trap with reflux condenser was placed 22 g (0.2 mole) catechol (Aldrich), 250 mL DMF, 64 g (0.4 mole+7.6 g excess) p-nitrofluorobenzene (Fluorochem), 80 g potassium carbonate (anhydrous) and 50 mL xylene. The mixture was refluxed under a nitrogen atmosphere for 5 hours, then, within 2.5 hours, 100 mL of liquid (xylene plus DMF) was distilled off and the hot liquid was poured into 2.0 l ice/water mixture with vigorous stirring. The resulting brown solid was filtered off and thoroughly washed with deionized water until neutral. The wet cake was boiled in 1200 mL ethanol and left to crystallize overnight to yield (including a second crop) 65 g (92.32% theoretical) of yellow crystals. Melting point 134°–135° C. Elemental analysis: Calc: C, 61.36%, H, 3.43%, 7.95%; Found: C, 61.34%, H, 3.43%, 7.92%.

B. Synthesis of 1,2-bis(4-aminophenoxy)benzene (POP amine)

In a 3 l round-bottomed flask equipped with a magnetic stirrer bar, reflux condenser and dropping funnel was placed 64.20 g (0.182 mol) of 1,2-bis(4-nitrophenoxy)benzene (SI-319), 700 mL ethanol and 2 g 5% palladium on charcoal. The mixture was brought to boil when 200 mL of hydrazine hydrate was added dropwise during a period of 1.5 hours. The mixture was refluxed for a further 3 hours. The hot mixture was then filtered over a filter agent and left to crystallize. The next day the crystals were separated and the liquid volume reduced to 400 mL, from which an additional crop of crystals was filtered off. The combined crystalline product was recrystallized twice from methanol/water (3:1) to yield 41.2 g of off-white crystals. By reducing the liquid volume a second crop of 5.7 g of crystals was obtained (overall yield 88.17% theoretical). Melting point 135°–136° C. Elemental analysis: Calc: C,. 73.95%, H, 5.51%, 9.59%; Found: C, 74.10%, H, 5.62%, 9.77%.

TABLE 1

| Example | Diacid | Diamine | Comments |
| --- | --- | --- | --- |
| 25A | POP | MPD | Fusible, forms fibres. Sol. DMF |
| 25B | MOM | PPD | Fusible, forms fibres. Sol. NMP |
| 25D | MOM | MPD | Forms fibres Sol. NMP |
| 25D | OOO | PPD | Forms fibres Sol. NMP |
| 25E | OOO | MPD | Forms fibres Sol. NMP |

PPD = para-phenylene diamine
MPD = meta-phenylene diamine

TABLE 2

| Ex. | Diacid chloride | Diamine | M. Wt. kg mol-1 | Tg/°C. | I.V./ (dl g-1) | TGA incipient wt. loss | TGA residue at 60°C. | Comments |
| --- | --- | --- | --- | --- | --- | --- | --- | --- |
| 26A | POP | PPD | 75 | 280 | 1.16 | 490 | 41 | Not fusible Sol. NMP |
| 26B | POP | MPD | 104 | 221 | 1.18 | 390 | 60 | Fusible, forms short fibres. Sol. NMP |
| 26C | POP | POP | 111 | 192 | 1.11 | 425 | 46 | Nonfusible Sol. NMP |
| 26D | MOM | MPD | | | | | | Long fibres Sol NMP |
| 26E | P3TBOP | PPD | | 250 | 0.70 | 415 | 55 | |
| | P3TBOP | MPD | | 217 | 0.54 | 380 | 47 | |
| 26G | P3TBOP | POP | | 194 | 0.32 | 420 | 44 | |
| 26H | PNOP | PPD | | 235 | 0.32 | 410 | 54 | |
| 26I | PNOP | MPD | | 246 | insol | 410 | 67 | |
| 26J | PNOP | POP | | 201 | 0.63 | 420 | 93 | |
| 26K | P35DTBOP | PPD | | 269 | 0.60 | 415 | 42 | |
| 26L | P35DTBOP | MPD | | 247 | 0.07 | 410 | 47 | |
| 26M | P3SDTB-OP | POP | | 218 | 0.65 | 420 | 40 | |
| 26N | IPA | POP | | | | | | Long fibres, Sol. NMP |
| 26O | TPA | POP | | | | | | Plastic melt, No fibres pulled Sol. NMP |
| 26P | IPA | MOM | | | | | | Long fibres, Sol. NMP |
| 26Q | TPA | MOM | | | | | | Non-fusible, no fibres Sol. NMP |

IPA = isophthalic acid;
TPA = terephthalic acid;
PPD = para-phenylene diamine;
MPD = meta-phenylene diamine.

TABLE 3

Polyarylates Formed by Transesterification

| Example | Diacid | Diacetate | Comments |
| --- | --- | --- | --- |
| 27A | POP | HQ | Sol. in boiling dichlorobenzene |
| 27B | POP | RES | V. sol. in THF. Fibres from melt. Solvent plasticised |
| 27C | MOM | HQ | Short brittle fibres from melt |
| 27D | P3TBOP | HQ | Sol. in chloroform, very long fibres from melt. |
| 27E | PNOP | HQ | Sol. in chloroform, long fibres from melt |
| 27F | P35DTBOP | HQ | Sol. in chloroform, long fibres from melt. |
| 28A | POP | HQ | Fusible, forms short fibres near decomp. temp. Sol NMP |

HQ = hydroquinone;
RES = resorcinol.

TABLE 4

Copolyarylates

| Example | Diacid | Other reagents | Comments |
|---|---|---|---|
| 29A | POP (0.25) | HQ (0.25), HBA (0.5) | Opaque soln. in NMP, fusible, long fibres from melt (>10 in), exhibits liquid crystallinity. |
| 29B | P3TBOP (0.15) | HQ (0.15), HBA (0.7) | Soluble in hot cresol, dichloroacetic acid, or NMP, opaque solutions, v. short fibres pulled from melt |

HBA = hydroxybenzoic acid;
HQ = diacetate of hydroquinone.

What is claimed is:

1. A compound of the formula

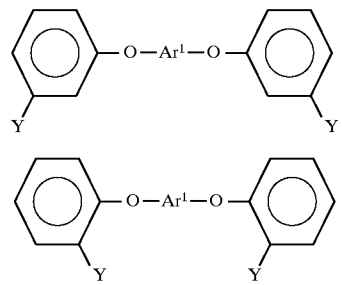

or

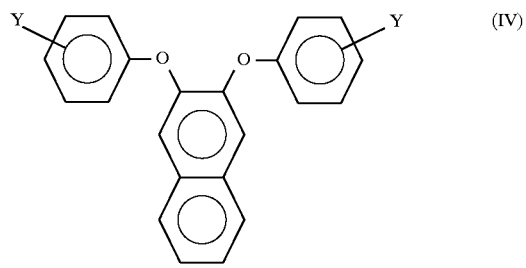

wherein:
Ar$_1$ is o-phenylene, alkyl-substituted o-phenylene, said alkyl having 1 to 20 carbon atoms, or halogen-substituted o-phenylene;
Y is —CN, —CO2H, CO2R$^1$ or COX;
R$^1$ is hydrocarbyl containing 1 to 20 carbon atoms; and
X is halogen.

2. The compound as recited in claim 1 which has the formula (II).

3. The compound as recited in claim 1 which has the formula (III).

4. The compound as recited in claim 1 which has the formula (IV).

5. The compound as recited in claim 1 wherein Ar$^1$ is o-phenylene.

6. The compound as recited in claim 1 wherein X is chlorine.

7. The compound as recited in claim 1 wherein R$^1$ contains 1 to 6 carbon atoms.

8. The compound as recited in claim 4 which is symmetrical.

* * * * *